United States Patent [19]

Leavitt

[11] 4,390,624

[45] Jun. 28, 1983

[54] PREPARATION OF PROLINE FROM ALGAE

[75] Inventor: Richard I. Leavitt, Baton Rouge, La.

[73] Assignee: Ethyl Corporation, Richmond, Va.

[21] Appl. No.: 329,224

[22] Filed: Dec. 10, 1981

[51] Int. Cl.$^3$ .................... C12P 13/24; C12R 1/89
[52] U.S. Cl. ................................ 435/107; 435/946
[58] Field of Search ........................ 435/107, 946

[56] References Cited

U.S. PATENT DOCUMENTS 4,224,409  9/1980  Nakamori et al. ............... 435/107

FOREIGN PATENT DOCUMENTS 56-10038   3/1981  Japan ................................ 435/107
1132036   10/1968  United Kingdom .

OTHER PUBLICATIONS

Aust. J. Plant Physiology 1979, vol. 6, pp. 69–79.
Limnol. Oceanographer, vol. 10, pp. 192–206, (1965).

*Primary Examiner*—Lionel M. Shapiro
*Attorney, Agent, or Firm*—Donald L. Johnson; John F. Sieberth; Willard G. Montgomery

[57] ABSTRACT

A process for producing L-proline in the absence of light by cultivating *Chlorella sp.* 580 algae in an aqueous growth medium containing a high concentration of sodium chloride of up to 1M in the final stage of cultivation and providing an adequate supply of carbon in the form of acetate ion, until algae of high L-proline content are obtained, harvesting the algae and thereafter recovering L-proline from the algae.

11 Claims, No Drawings

PREPARATION OF PROLINE FROM ALGAE

BACKGROUND OF THE INVENTION

This invention relates to a process for producing L-proline. More particularly, it relates to a process for the production of L-proline in high yields in the absence of light by cultivation and work-up of a certain type of algae, specifically *Chlorella sp.* 580. Conditions of cultivation and work-up are defined.

L-proline is a useful amino acid which is used as a medicine and in other applications. In the past, L-proline has been produced mainly by isolation from hydrolysates of proteins or gelatin or by organic synthesis. However, the yield of product obtained by these methods is very low, and the procedures involved are complicated. As a result, L-proline is one of the most expensive amino acids. Therefore, the development of a process for the mass production of L-proline using inexpensive starting materials would be highly desirable.

The fact that L-proline is contained in algae of the genus Chlorella is known. Further, it is known that L-proline is produced by the Chlorella algae in response to the environment in which it is grown i.e. the sodium chloride content of the growth medium. The relationship between L-proline cell accumulation is *Chlorella emersonii* and sodium chloride content of the environment external to the cell has been described in *AUST. J Plant Physiology* (1979) 6, 69–79 in which it was reported that in the *emersonii* species of Chlorella, L-proline production within the cell generally increases as the sodium chloride concentration is increased in the environment external to the cell. However, it appears that only small amounts of L-proline are produced within *Chlorella emersonii* and, at sodium chloride concentrations higher than 335mM, the cells plasmolyze.

The fact that Chlorella sp. 580 excrete proline also is known as reported in Limnol. Oceanographer (1965) 10:192–206. However, the excretion levels reported therein also are small.

Methods for producing L-proline by fermentation also are known. For example, British 1,132,036 discloses that L-proline can be produced from mutant strains of *Micrococcus glutamicus* by fermentation. Also U.S. Pat. No. 4,224,409 discloses that L-proline can be obtained by culturing a mutant of the genus Brevibacterium, Corynebacterium or Microbacterium. L-proline production by fermentation, however, is somewhat expensive since the sources of carbon for use in the fermentation medium include carbon sources other than $CO_2$, such as, for example, pentoses, hexoses, disaccharides, or the like.

Thus, even though it is known that L-proline can be produced both intracellularly and extracellularly by the genus Chlorella, insofar as Applicant is aware, nothing has been reported in the literature with respect to the identification of a specific species of Chlorella and a specific method of cultivating said specific organism such that L-proline can be produced intracellularly within the organism in amounts high enough to be considered sufficient to form the basis for an industrial process.

In Applicant's co-pending U.S. application Ser. No. 329,226, filed Dec. 10, 1981, entitled *Process for the Preparation of Amino Acids*, Applicant has identified both a specific species of Chlorella, namely Chlorella sp. 580, and a method of cultivating the species to produce L-proline in amounts high enough to be considered sufficient to form the basis for commercial production. According to Applicant's process disclosed therein, Chlorella sp. 580 is cultivated under high-intensity illumination in an aqueous growth medium containing a high concentration of sodium chloride of at least 1M in the final stage of cultivation, in the presence of an adequate supply of carbon, in a depth not exceeding approximately 20 cm of the aqueous medium, until algae of high L-proline content are obtained. The algae are then harvested and L-proline is thereafter recovered from the algae. While Applicant's aforedescribed process does provide for the accumulation of high amounts of L-proline within Chlorella sp. 580 algae cells (up to approximately 35% of the cell weight), cultivation of the algae must be carried out under high-intensity illumination because the process uses as its carbon source, carbon dioxide. That is, fixation of $CO_2$ by the algae to make cellular material, including L-proline, requires the presence of light. At high cell densities, however, light becomes limiting in that as the cell density of the culture progressively increases during growth, it becomes increasingly more difficult for the light to penetrate the cell mass. This results in a disruption in cell growth and a subsequent decrease in proline production due to the diminished ability of the algae to transform $CO_2$ into proline due to the lack of light. Thus, it would be highly desirable to supply the cells with a source of carbon which would either supplement or replace $CO_2$ as a source of proline as the amount of light available to the algae decreases or becomes absent altogether.

SUMMARY OF THE INVENTION

In accordance with the present invention, Applicant has achieved production of L-proline in high quantities within Chlorella sp. 580 in the absence of light in the following manner.

As disclosed in Applicant's aforementioned U.S. application Ser. No. 329,227, filed Dec. 10, 1981, entitled *Process for the Preparation of Amino Acids*, Applicant has found that the production of high quantities of L-proline in Chlorella sp. 580 algae can be brought about by increasing the salinity of its growth medium. That is, the algae are cultured for a period of time in a growth medium containing a relatively low concentration of sodium chloride such as, for example, from about 0.25 to about 0.5M NaCl, and preferably 0.5M NaCl, and then the algae are stressed by increasing the salinity of the growth medium whereby excess amounts of L-proline are produced within the algae cells.

The production of L-proline thus can be broken down into two phases. In the first phase, or the growth phase, the algae are added to a suitable growth medium (supplemented tap or sea-water) at low density and allowed to divide and increase their cell number and mass for a period of time, normally from about three to twenty-one days, until they have reached a cell density of from about 250 to about 5000mg/1 based on dry cell weight. Upon reaching the aforementioned cell density, the algae are then transferred promptly to a culture medium having a higher concentration of sodium chloride and the cells are then made proline productive by continued incubation without growth for an additional period of time from about 6 to 80 hours, typically 16 hours. This is the second phase, or proline production phase of the process. In lieu of transferring the algae from one medium having a lower sodium chloride concentration to a second and separate medium containing a higher sodium chloride concentration, the sodium chloride content of the original growth medium can simply be increased to a higher concentration at the end of the growth phase. For optimal growth and proline production, growth is carried out in the presence of approximately 0.5M sodium chloride followed by proline production in the presence of 1M sodium chloride.

While the first phase or growth phase of the process must be carried out under high-intensity illumination using $CO_2$ as a carbon source, Applicant has found that the second or proline production phase of the process can be carried out in the absence of light by replacing $CO_2$ as a source of proline manufacture with acetate. Thus, even though the cell density of the culture increases to a point where there is insufficient light for the cells to effectively or efficiently utilize $CO_2$ as a source of proline manufacture, proline production can be carried out without interruption within the cells in the absence of light by substituting acetate as a source of proline in place of $CO_2$. Further, Applicant has found thus far that there appears to be no need to stress the cells by increasing the salt concentration of the medium during the proline production phase of the process in order to produce excess amounts of proline within the cells as must be done when the entire process is carried out under high-intensity illumination. That is, Applicant has found that the amount of proline produced when acetate is used as a carbon source during the proline production phase of the process is not increased by an increase in the salt or sodium chloride concentration in the aqueous medium in which the cells are cultured. Thus far, it has been found that maximum proline production occurs in an aqueous medium containing approximately 0.5M sodium chloride. Increasing the sodium chloride concentration to 1 molar does not produce any more proline than is produced at 0.5 molar concentration.

DESCRIPTION OF THE PREFERRED EMBODIMENT

Thus, a preferred embodiment of the present invention is a process for the production of L-proline in high amounts which comprises cultivating *Chlorella sp.* 580 algae under high-intensity illumination in an aqueous growth medium containing an amount sufficient of nutrients including nitrogen to effect growth of the algae and a high concentration of sodium chloride of up to 1M under an aerobic condition, providing an adequate supply of carbon in the form of carbon dioxide, in a depth not exceeding approximately 20cm of the aqueous medium, for a period of time until the density of the algae substantially prevents the utilization of $CO_2$ by the algae to produce L-proline and thereafter continuing to culture the algae in the absence of light and carbon dioxide while providing acetate ion to the medium in an amount sufficient to produce high amounts of L-proline within the algae for a period of time until algae of high L-proline content are obtained, harvesting the algae and recovering from same the L-proline thus produced.

The algae used in the process of the invention are designated Chlorella sp. 580 which belong to the Class of Chlorellaceae, Order of Chlorophyta. The algae are unicellular, non-motile, non-nitrogen fixing cells which are found to oval in shape. The cells are approximately 5 to 10 μm in diameter and have a rigid cell wall. Under optimum conditions of cultivations, the L-proline content of each cell can be increased to approximately 15% to about 35% of the cell weight, or from about 150 mg to about 350mg per gram dry weight of algae. Cultivation is carried out either on an artificial medium or on sea-water adjusted so as to contain the required nutrients and salt concentration. The aqueous culture medium employed in the present invention contains an assimilable carbon source, specifically $CO_2$ in the light dependent phase of cultivation, and acetate ion, in the proline production phase or light independent phase of cultivation. Assimilable nitrogen sources, conventional inorganic salts, such as for example, the phosphates, sulfates, nitrates, chlorides, and other salts of potassium, sodium, calcium, magnesium, iron, zinc, manganese, cobalt, copper, etc., and, if necessary, minor organic nutrients such as vitamins or the like, also are employed in the medium. Such nutrients are well known in the art.

During the growth phase or the light dependent phase of cultivation, cultivation is under an adequately high intensity of illumination and can be carried out either outdoors in sunlight or artificial light may be used if desired. If artificial light is used, the intensity of illumination should be at least 200f.c. to 1000f.c., and preferably about 300f.c. When cultivated outdoors, the depth of the water should not exceed about 20cm, and the optimum depth is from about 7cm to about 15cm.

As a nitrogen source, various kinds of inorganic or organic salts or compounds such as potassium nitrate, sodium nitrate, ammonia, ammonium sulfate, ammonium chloride, ammonium nitrate or ammonium carbonate may be used. Mixtures of these substances also may be used.

As indicated above, it is possible to use sea-water augmented by the addition of various nutrient constituents, aforedisclosed, or concentrated by partial evaporation and addition of certain aforedisclosed constituents. If supplemented sea-water is used, it should have a sodium chloride content sufficient for the prouction of L-proline in high amounts, preferably from about 0.25M to 1M sodium chloride, supplemented with a nitrogen source such as $NaNO_3$, 50mg/l to 1.0g/l, and a phosphate source such as $K_2HPO_4$, 15mg/l to 300mg/l.

During the proline production phase or the light independent phase of cultivation, there must be provided an adequate and suitable source of carbon. A 5% $CO_2$ enriched atmosphere has been found to be optimum. However, a 1% to 15% $CO_2$ enriched atmosphere can be used if desired.

In order for the proline production phase of the process to be carried out in the absence of light, there must be provided a carbon source which is not light dependent for assimilation by the cells. Applicant has found that the substitution of acetate ion for $CO_2$ in amounts ranging from approximatley 0.003% to about 3.0% by weight based on the total weight of the medium constituents provides a suitable carbon source that will permit production of L-proline in high quantities within the algae cells in the absence of light. Sodium acetate is the preferred acetate ion source, however, other sources including potassium acetate, ammonium acetate and the like may be used.

Biotin and vitamins such as thiamine and cyanocobalamin also may be used in the medium.

As noted previously, the medium should contain between approximately 0.25M and 1M NaCl, preferably 0.5M NaCl.

Culturing is carried out under an aerobic condition, such as aerobic shaking of the culture or stirring of a submerged culture with introduction of air thereinto at a temperature of from about 10° C. to about 40° C., preferably from about 25° C. to about 35° C., and at a pH of about 7.0 to about 9.0. An optimum pH is about 8.0. The pH is advantageously adjusted by adding quantities of alkali or mineral acids such as hydrochloric acid or nitric acid as required.

Thus, the production of high quantities of L-proline in Chlorella sp. 580 is brought about by culturing the algae under high-intensity illumination, in the presence of $CO_2$ in accordance with the aforediscussed procedure until the algae reach a cell density at which the availability of light becomes limiting to the point that the algae can no longer utilize $CO_2$ as a source for subsequent proline production. Applicant has found that this occurs typically upon reaching a cell density of approximately 5g/l. However, this should not be considered as an absolute standard by which to gauge ineffective or inefficient $CO_2$ utilization by the cells since this point may occur somewhere above or below 5g/l depending on the prevailing conditions. Instead, one should consider a cell density of 5g/l to be that point at which it can be assured with a fair amount of certainty that $CO_2$ can not be used by the cells as a source for proline production. At this point, acetate is then substiuted for $CO_2$ as a source of carbon for proline production with proline production proceeding in the absence of light until algae of high proline content are obtained. Typically, the cells reach a density of approximately 5g/l after three to twenty-one days of growth under the aforedescribed conditions. Proline production is generally complete within 6 to 80 hours, typically after 16 hours, of incubation in the presence of acetate ion.

After completion of culturing and proline production, the cells are harvested (separated from the culture liquor) and the proline is recovered from the cells.

Harvesting can be accomplished by conventional methods such as sedimentation, filtration or centrifugation. Optionally, a flocculant may be added to the aqueous culture to concentrate the cells into a singular mass prior to settling or the implementation of any of the other aforementined harvesting techniques. Alumina has been found to be a particularly effective flocculant. Suitable sources of $Al^{+3}$ flocculant are aluminum salts such as $Al(NO_3)_3.9H_2O$; $Al_2(SO_4)_3.10H_2O$; $AlNH_4(SO_4)_2.10H_2O$ and $Al_2(SO_4)_3.18H_2O$. In general, the addition of from about 5 to about 100 ppm of $Al^{+3}$ to a typical cell suspension is sufficient to bring about a 10 fold to 100 fold increase in density (g/l) of the cells. Flocculation is generally complete within 1 to 5 minutes, and essentially complete clarification of the culture liquor is achieved within 1 to 24 hours.

After harvesting, the cells are suspended in water and heated to above 80° C., typically 100° C., for a period of time of up to about 1 hour, whereupon the L-proline accumulated within the cells is released from the cells into the water. L-proline is then recovered from the water phase by any known methods such as by using ion-exchange resin, acid or alcohol extraction.

Optionally, L-proline can be recovered simply by harvesting the cells as described above to remove the culture liquor therefrom and subsequently reducing the molarity of the sodium chloride concentration originally added in order to achieve maximum proline production by suspending the cells in fresh water in an amount sufficient to cause release of the proline into the water phase. Cell concentrates made proline-rich by the addition of sodium chloride can be made to release up to 100% of their proline by simple dilution of the sodium chloride solution with fresh water. Partial release occurs when the salt concentration is reduced below 0.3M and generally complete release occurs at dilutions below 0.14M sodium chloride. Dilution recovery is carried out at room temperature.

The proline is recovered and purified by conventional methods such as ion-exchange chromatography, thin layer chromatography, gas chromatography and obtained in crystalline form.

Typically, amino acids other than L-proline are present in the extract or water phase following proline release from the cells. The total amount of non-proline amino acids can range up to as high as 10 weight percent with alanine typically being present in the highest amounts.

The following example is given merely as illustrative of the present invention and is not to be considered as limiting.

EXAMPLE

An aqueous medium (deionized water) was prepared containing 0.017g/l $K_2HPO_4$, 0.340g/l $NaNO_3$, 0.100g/l $KNO_3$, 0.043g/l $NaHCO_3$, 5.95g/l $MgSO_4.7H_2O$, 4.10g/l $MgCl_2$, 1.47g/l $CaCl_2$, 0.00024g/l $FeCl_3$, 0.00011g/l $ZnCl_2$, 0.0114g/l ethyl-enediamine tetraacetic acid, 0.00104g/l $H_3BO_3$, 0.00126g/l $MnCl_2$, 0.00000473g/l $CoCl_2$, 0.000000266g/l $CuCl_2$, 0.0002g/l thiamine-HCL, 0.000001g/l biotin, and 0.000001g/l cyanocbalamin. A 20ml aliquot of the aqueous medium was placed into each of six 125ml flasks. In flasks designated nos. 1, 3 and 5 (culture nos. 1, 3 and 5 in the table below), 0.5M NaCl was added to each medium. Each medium was inoculated with 50mg/l Chlorella sp. 580 which had previously been cultured at approximately 30° C. for about 72 hours in a 5% $CO_2$ enriched atmosphere with shaking under a bank of fluorescent lights at an average luminescence of 300 foot candle power in an aqueous medium containing the aforedescribed constituents and 0.5M NaCl. The lights were located approximately 30cm from the surface of the culture. The pH was maintained between 7.0 and 9.0 by adding $CO_2$. After inoculation, each culture then was incubated at 30° C. for 16 hours with shaking. The pH of each culture medium again was maintained between 7.0 and 9.0. The cells in flasks nos. 1 and 2 were incubated in the presence of light supplied by a bank of fluorescent lights at an average luminescence of 300 candle foot power in the aforementioned manner. The cells in flasks nos. 3–6 were incubated in the dark. The cells in flasks nos. 1–4 were incubated in a 5% carbon dioxide enriched atmosphere. The cells in flasks nos. 5 and 6 were not incubated in the presence of carbon dioxide, however, 0.6% by weight sodium acetate was added to the culture medium in flasks nos. 5 and 6. The results are set forth in the table below.

TABLE

| Culture No. | Carbon Source | Illumination | (NaCl) M | mg Proline mg/cell |
|---|---|---|---|---|
| 1 | 5% $CO_2$/air | 300cf power | .5 | .22 |
| 2 | 5% $CO_2$/air | 300cf power | 1.0 | .40 |
| 3 | 5% $CO_2$/air | Dark | .5 | .11 |
| 4 | 5% $CO_2$/air | Dark | 1.0 | .24 |
| 5 | 0.6% Sodium acetate | Dark | .5 | .48 |
| 6 | 0.6% Sodium acetate | Dark | 1.0 | .48 |

As demonstrated in the table, when light was eliminated from the culture, proline levels were reduced by 50% in the presence of 0.5M NaCl and approximately 40% in the presence of 1M NaCl. This can be seen by contrasting culture No. 1 with culture No. 3 and culture No. 2 with culture No. 4 in the table. In contrast to this reduction in the dark, the addition of 0.6 weight percent sodium acetate to culture Nos. 5 and 6 increased the proline content of the cells to approximately 48 percent of the cell weight at 0.5M NaCl concentration. This level was the maximum level obtained, however, and was not further increased by increase in the molarity of sodium chloride in the medium to 1.0 as demonstrated by culture No. 6 in the table.

I claim

1. A process for the production of L-proline in high amounts which comprises cultivating Chlorella sp. 580 algae under high intensity illumination in an aqueous growth medium containing an amount sufficient of nutrients including nitrogen to effect growth of the algae and a high concentration of sodium chloride of up to 1M under an aerobic condition, providing an adequate supply of carbon in the form of $CO_2$ in a depth not exceeding approximately 20cm of the aqueous medium for a period of time until the density of the algae substantially prevents the utilization of $CO_2$ by the algae to produce L-proline and thereafter continuing to cultivate the algae in the absence of light and $CO_2$ while providing acetate ion to the medium in an amount sufficient to produce high amounts of L-proline within the algae for a period of time until algae of high L-proline content are obtained, harvesting the algae and recovering from same the L-proline thus produced.

2. A process according to claim 1, wherein said aqueous growth medium is an artificial growth medium containing:
0.017g/l $K_2HPO_4$, 0.340g/l $NaNO_3$, 0.100g/l $KnO_3$, 0.043g/l $NaHCO_3$, 5.95g/l $MgSO_4.7H_2O$, 4.10g/l $MgCl_2$, 1.47g/l $CaCl_2$, 0.00024g/l $FeCl_3$, 0.00011g/l $ZnCl_2$, 0.0114g/l ethylenediamine tetraacetic acid, 0.00104g/l $H_3BO_3$, 0.00126g/l $MnCl_2$, 0.00000473g/l $CoCl_2$, 0.000000266g/l $CuCl_2$, 0.0002g/l thiamine-HCL, 0.000001g/l biotin, and 0.000001g/l cyanocobalamin.

3. A process according to claim 1, wherein cultivation is carried out at a temperature of from about 10° C. to about 40° C.

4. A process according to claim 1, wherein the source of said high-intensity illumination is sunlight.

5. A process according to claim 1, wherein said source of high-intensity ilumination is artificial light.

6. The process according to claim 5, wherein the intensity of illumination is between from about 200f.c. to 1000f.c.

7. A process according to claim 1, wherein said algae are cultivated in the presence of high-intensity illumination for a period of time from about 3 to 21 days.

8. A process according to claim 1, wherein said algae are cultivated in the presence of high-intensity illumination until said algae attain a cell density of up to at least 5g/l.

9. A process according to claim 1, wherein said algae are cultivated in the absence of light and $CO_2$ for a period of time from about 6 to 80 hours.

10. A process according to claim 1, wherein the amount of acetate ion present in the medium ranges between about 0.003% to about 3.0% by weight based on the total weight of the medium constituents.

11. A process according to claim 1, wherein the algae are harvested by sedimentation.

* * * * *